(12) United States Patent
Berg

(10) Patent No.: US 10,159,476 B2
(45) Date of Patent: Dec. 25, 2018

(54) METHOD FOR SECURING SUTURES TO BONES

(71) Applicant: Lumaca Orthopaedics Pty Ltd, Carlton (AU)

(72) Inventor: Jeffery H. Berg, Ashburn, VA (US)

(73) Assignee: Lumaca Orthopaedics Pty Ltd, Victoria (AU)

( * ) Notice: Subject to any disclaimer, the term of this patent is extended or adjusted under 35 U.S.C. 154(b) by 0 days.

(21) Appl. No.: 14/730,167

(22) Filed: Jun. 3, 2015

(65) Prior Publication Data

US 2015/0265327 A1 Sep. 24, 2015

Related U.S. Application Data

(62) Division of application No. 13/252,494, filed on Oct. 4, 2011, which is a division of application No. 12/453,290, filed on May 6, 2009.

(Continued)

(51) Int. Cl.
*A61B 17/04* (2006.01)
*A61B 17/86* (2006.01)
(Continued)

(52) U.S. Cl.
CPC .......... *A61B 17/0401* (2013.01); *A61B 17/86* (2013.01); *A61B 17/864* (2013.01); *A61B 17/8645* (2013.01); *A61B 17/8685* (2013.01); *A61B 17/88* (2013.01); *A61B 17/8872* (2013.01); *A61B 17/8875* (2013.01);
(Continued)

(58) Field of Classification Search
CPC ........ A61B 17/0401; A61B 2017/0409; A61B 2017/0412; A61B 2017/0414; A61B 2017/044; A61B 2017/0445; A61B 2017/0446; A61B 2017/0448; A61B 17/86; A61B 17/864; A61B 17/8645; A61B 17/8685; A61B 17/88; A61B 17/8872; A61B 17/8875; A61B 17/8897
See application file for complete search history.

(56) References Cited

U.S. PATENT DOCUMENTS

| | | | |
|---|---|---|---|
| 4,532,926 | A | 8/1985 | O'Holla |
| 4,784,126 | A | 11/1988 | Hourahane |

(Continued)

FOREIGN PATENT DOCUMENTS

| | | |
|---|---|---|
| EP | 1006948 | 6/2000 |
| WO | WO2010121271 | 10/2010 |

OTHER PUBLICATIONS

Arthrex, Inc., "Speed and Precision in Knotless Rotator Cuff Repair," at least as early as Apr. 18, 2010.

(Continued)

*Primary Examiner* — Larry E Waggle, Jr.
(74) *Attorney, Agent, or Firm* — Morriss O'Bryant Compagni Cannon, PLLC

(57) ABSTRACT

A method for securing a repair, such as a rotator cuff repair and includes an anchor placed within a hole formed in bone and a cannulated screw inserted into the hole after the anchor has been inserted to effectuate a firm and secure connection of tissue to bone, particularly when the quality of the bone does not permit optimal fixation. The method allows superior tissue fixation to bone with the ease of knotless suture anchor application.

23 Claims, 15 Drawing Sheets

Related U.S. Application Data

(60) Provisional application No. 61/071,563, filed on May 6, 2008.

(51) Int. Cl.
*A61B 17/88* (2006.01)
*A61B 90/00* (2016.01)

(52) U.S. Cl.
CPC ...... *A61B 17/8897* (2013.01); *A61B 17/0469* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61B 2017/0446* (2013.01); *A61B 2017/0448* (2013.01); *A61B 2090/062* (2016.02); *A61B 2217/00* (2013.01)

(56) References Cited

U.S. PATENT DOCUMENTS

| | | |
|---|---|---|
| 4,950,270 A | 8/1990 | Bowman et al. |
| 5,037,422 A | 8/1991 | Hayhurst et al. |
| 5,062,843 A | 11/1991 | Mahony, III |
| 5,100,417 A | 3/1992 | Cerier et al. |
| 5,102,421 A | 4/1992 | Anspach, Jr. |
| 5,116,337 A | 5/1992 | Johnson |
| 5,167,664 A | 12/1992 | Hodorek |
| 5,176,682 A | 1/1993 | Chow |
| 5,236,445 A | 8/1993 | Hayhurst et al. |
| 5,258,016 A | 11/1993 | DiPoto et al. |
| 5,268,001 A | 12/1993 | Nicholson et al. |
| 5,269,809 A | 12/1993 | Hayhurst et al. |
| 5,282,802 A | 2/1994 | Mahony, III |
| 5,354,300 A | 10/1994 | Goble et al. |
| 5,366,457 A | 11/1994 | McGuire et al. |
| 5,370,662 A | 12/1994 | Stone et al. |
| 5,372,599 A | 12/1994 | Martins |
| RE34,871 E | 3/1995 | McGuire et al. |
| 5,409,486 A | 4/1995 | Reese |
| 5,423,860 A | 6/1995 | Lizardi et al. |
| 5,464,427 A | 11/1995 | Curtis et al. |
| 5,472,452 A | 12/1995 | Trott |
| 5,486,197 A | 1/1996 | Le et al. |
| 5,496,326 A | 3/1996 | Johnson |
| 5,545,180 A | 8/1996 | Le et al. |
| 5,584,835 A | 12/1996 | Greenfield |
| 5,601,557 A | 2/1997 | Hayhurst |
| 5,632,748 A | 5/1997 | Beck, Jr. et al. |
| 5,643,320 A | 7/1997 | Lower et al. |
| 5,645,589 A | 7/1997 | Li |
| 5,647,874 A | 7/1997 | Hayhurst |
| 5,674,224 A | 10/1997 | Howell et al. |
| 5,681,352 A | 10/1997 | Clancy, III et al. |
| 5,683,418 A | 11/1997 | Luscombe et al. |
| 5,707,395 A | 1/1998 | Li |
| 5,720,753 A | 2/1998 | Sander et al. |
| 5,720,765 A | 2/1998 | Thal |
| 5,725,529 A | 3/1998 | Nicholson et al. |
| 5,728,136 A | 3/1998 | Thal |
| 5,733,307 A | 3/1998 | Dinsdale |
| 5,741,300 A | 4/1998 | Li |
| 5,755,718 A | 5/1998 | Sklar |
| 5,814,072 A | 9/1998 | Bonutti |
| 5,860,978 A | 1/1999 | McDevitt et al. |
| 5,871,504 A | 2/1999 | Eaton et al. |
| 5,876,455 A | 3/1999 | Harwin |
| 5,895,425 A | 4/1999 | Grafton et al. |
| 5,899,938 A | 5/1999 | Sklar et al. |
| 5,906,632 A | 5/1999 | Bolton |
| 5,911,721 A | 6/1999 | Nicholson et al. |
| 5,916,216 A | 6/1999 | DeSatnick et al. |
| RE36,289 E | 8/1999 | Le et al. |
| 5,931,869 A | 8/1999 | Boucher et al. |
| 5,935,129 A | 8/1999 | McDevitt et al. |
| 5,957,953 A | 9/1999 | DiPoto et al. |
| 5,961,520 A | 10/1999 | Beck, Jr. et al. |
| 5,961,538 A | 10/1999 | Pedlick et al. |
| 5,968,044 A | 10/1999 | Nicholson et al. |
| 5,968,045 A | 10/1999 | Frazier |
| 6,022,373 A | 2/2000 | Li |
| 6,024,758 A | 2/2000 | Thal |
| 6,045,574 A | 4/2000 | Thal |
| 6,048,343 A | 4/2000 | Mathis et al. |
| 6,099,530 A | 8/2000 | Simonian et al. |
| 6,146,406 A | 11/2000 | Shluzas et al. |
| 6,149,669 A | 11/2000 | Li |
| 6,159,235 A | 12/2000 | Kim |
| 6,264,694 B1 | 7/2001 | Weiler |
| 6,290,711 B1 | 9/2001 | Caspari et al. |
| 6,402,757 B1 | 6/2002 | Moore, III et al. |
| 6,508,830 B2 | 1/2003 | Steiner |
| 6,517,542 B1 | 2/2003 | Papay et al. |
| 6,527,795 B1 | 3/2003 | Lizardi |
| 6,544,281 B2 | 4/2003 | ElAttrache et al. |
| 6,599,289 B1 | 7/2003 | Bojarski et al. |
| 6,635,073 B2 | 10/2003 | Bonutti |
| 6,641,596 B1 * | 11/2003 | Lizardi .............. A61B 17/0401 606/232 |
| 6,679,917 B2 * | 1/2004 | Ek ................... A61B 17/0401 623/20.14 |
| 6,716,234 B2 | 4/2004 | Grafton et al. |
| 6,778,861 B1 | 8/2004 | Liebrecht et al. |
| 6,916,321 B2 | 7/2005 | TenHuisen et al. |
| 6,984,241 B2 | 1/2006 | Lubbers et al. |
| 7,008,451 B2 | 3/2006 | Justin et al. |
| 7,022,129 B2 | 4/2006 | Overaker et al. |
| 7,118,581 B2 | 10/2006 | Friden |
| 7,141,066 B2 | 11/2006 | Stiner et al. |
| 7,144,413 B2 | 12/2006 | Wilford et al. |
| 7,172,595 B1 | 2/2007 | Goble |
| 7,201,773 B2 | 4/2007 | Steiner et al. |
| 7,235,100 B2 | 6/2007 | Martinek |
| 7,320,701 B2 | 1/2008 | Haut et al. |
| 7,485,136 B2 | 2/2009 | Chan |
| 7,637,949 B2 | 12/2009 | Hart |
| 7,648,524 B2 | 1/2010 | Zhang et al. |
| 7,651,528 B2 | 1/2010 | Montgomery et al. |
| 7,803,173 B2 | 9/2010 | Burkhart et al. |
| 7,837,731 B2 | 11/2010 | Sklar |
| 7,857,817 B2 | 12/2010 | Tallarida et al. |
| 7,867,251 B2 | 1/2011 | Colleran et al. |
| 7,867,264 B2 * | 1/2011 | McDevitt ............ A61B 17/0642 606/301 |
| 7,875,056 B2 | 1/2011 | Jervis et al. |
| 7,951,198 B2 | 5/2011 | Sucec et al. |
| 7,955,388 B2 | 6/2011 | Jensen et al. |
| 8,066,713 B2 | 11/2011 | DiMauro et al. |
| 8,110,001 B2 | 2/2012 | Carter et al. |
| 8,128,658 B2 | 3/2012 | Kaiser et al. |
| 8,529,610 B2 | 9/2013 | Graf et al. |
| 2002/0007182 A1 | 1/2002 | Kim |
| 2002/0040241 A1 | 4/2002 | Jarvinen |
| 2002/0072797 A1 | 6/2002 | Hays et al. |
| 2002/0161401 A1 | 10/2002 | Stiner |
| 2002/0188298 A1 | 12/2002 | Chan |
| 2003/0065332 A1 | 4/2003 | TenHuisen et al. |
| 2003/0065361 A1 | 4/2003 | Dreyfuss |
| 2003/0088251 A1 | 5/2003 | Braun et al. |
| 2003/0088272 A1 | 5/2003 | Smith |
| 2003/0105489 A1 | 6/2003 | Eichhorn et al. |
| 2003/0130695 A1 | 7/2003 | McDevitt et al. |
| 2003/0171811 A1 | 9/2003 | Steiner et al. |
| 2003/0216780 A1 | 11/2003 | Fitts et al. |
| 2004/0068262 A1 | 4/2004 | Lemos et al. |
| 2004/0093031 A1 * | 5/2004 | Burkhart ............ A61B 17/0401 606/232 |
| 2004/0111117 A1 | 6/2004 | Colleran et al. |
| 2004/0133239 A1 | 7/2004 | Singhatat |
| 2004/0153076 A1 | 8/2004 | Singhatat et al. |
| 2004/0267361 A1 | 12/2004 | Donnelly et al. |
| 2005/0075668 A1 * | 4/2005 | Lizardi .............. A61B 17/0401 606/232 |
| 2005/0171546 A1 | 8/2005 | Wolf |
| 2005/0177165 A1 | 8/2005 | Zang et al. |

(56) References Cited

U.S. PATENT DOCUMENTS

| | | | |
|---|---|---|---|
| 2005/0267478 A1 | 12/2005 | Corradi et al. | |
| 2006/0079904 A1 | 4/2006 | Thal | |
| 2006/0095130 A1 | 5/2006 | Caborn et al. | |
| 2006/0259076 A1 | 11/2006 | Burkhart et al. | |
| 2006/0276841 A1* | 12/2006 | Barbieri | A61B 17/0401 606/232 |
| 2007/0055255 A1 | 3/2007 | Siegel | |
| 2007/0115805 A1 | 5/2007 | Ge et al. | |
| 2007/0162002 A1 | 7/2007 | Tornier | |
| 2007/0225719 A1* | 9/2007 | Stone | A61B 17/0401 606/232 |
| 2007/0225805 A1 | 9/2007 | Schmieding | |
| 2008/0004626 A1 | 1/2008 | Glazer et al. | |
| 2008/0065114 A1 | 3/2008 | Stone et al. | |
| 2008/0132956 A1 | 6/2008 | Biedermann et al. | |
| 2008/0154314 A1 | 6/2008 | McDevitt | |
| 2008/0183290 A1 | 7/2008 | Baird et al. | |
| 2008/0208253 A1 | 8/2008 | Dreyfuss et al. | |
| 2008/0234730 A1 | 9/2008 | Cotton et al. | |
| 2008/0275469 A1 | 11/2008 | Fanton et al. | |
| 2008/0275554 A1 | 11/2008 | Iannarone et al. | |
| 2008/0306511 A1 | 12/2008 | Cooper et al. | |
| 2008/0319546 A1 | 12/2008 | Bojarski et al. | |
| 2009/0187216 A1 | 7/2009 | Schmieding et al. | |
| 2009/0192608 A1 | 7/2009 | Paulos | |
| 2009/0216326 A1 | 8/2009 | Hirpara et al. | |
| 2009/0254090 A1 | 10/2009 | Lizee | |
| 2009/0281581 A1 | 11/2009 | Berg | |
| 2009/0287259 A1 | 11/2009 | Trenhaile et al. | |
| 2009/0299386 A1 | 12/2009 | Meridew | |
| 2009/0312794 A1 | 12/2009 | Nason et al. | |
| 2009/0312795 A1 | 12/2009 | Barbieri et al. | |
| 2009/0318959 A1 | 12/2009 | Burkhart | |
| 2010/0016893 A1 | 1/2010 | Fanton | |
| 2010/0049258 A1 | 2/2010 | Dougherty | |
| 2010/0063541 A1 | 3/2010 | Brunelle et al. | |
| 2010/0069958 A1 | 3/2010 | Sullivan et al. | |
| 2010/0145395 A1 | 6/2010 | Graf et al. | |
| 2010/0152773 A1 | 6/2010 | Lunn et al. | |
| 2010/0160962 A1 | 6/2010 | Dreyfuss et al. | |
| 2010/0161055 A1 | 6/2010 | Donnelly et al. | |
| 2010/0174369 A1 | 7/2010 | Wang et al. | |
| 2010/0179592 A1 | 7/2010 | Martinek et al. | |
| 2010/0185238 A1 | 7/2010 | Cauldwell et al. | |
| 2010/0217389 A1 | 8/2010 | Cheng et al. | |
| 2010/0241124 A1 | 9/2010 | Housman et al. | |
| 2010/0249833 A1 | 9/2010 | Dreyfuss | |
| 2010/0249930 A1 | 9/2010 | Myers | |
| 2010/0262184 A1 | 10/2010 | Dreyfuss | |
| 2010/0298888 A1 | 11/2010 | Graf et al. | |
| 2010/0331881 A1 | 12/2010 | Hart | |
| 2011/0004242 A1 | 1/2011 | Stchur | |
| 2011/0015675 A1 | 1/2011 | Howard et al. | |
| 2011/0054526 A1 | 3/2011 | Stone et al. | |
| 2011/0087283 A1 | 4/2011 | Donnelly et al. | |
| 2011/0106252 A1 | 5/2011 | Barwood et al. | |
| 2011/0106253 A1 | 5/2011 | Barwood et al. | |
| 2011/0112641 A1 | 5/2011 | Justin et al. | |
| 2011/0152930 A1 | 6/2011 | Howe | |
| 2011/0184516 A1 | 7/2011 | Baird et al. | |
| 2011/0184517 A1 | 7/2011 | Baird et al. | |
| 2011/0196490 A1 | 8/2011 | Gadikota et al. | |
| 2011/0251688 A1 | 10/2011 | Sklar | |
| 2011/0264140 A1 | 10/2011 | Lizardi et al. | |
| 2011/0276092 A1 | 11/2011 | Dreyfuss | |
| 2011/0282449 A1 | 11/2011 | Montgomery et al. | |
| 2011/0313453 A1 | 12/2011 | Krumme et al. | |
| 2012/0016415 A1 | 1/2012 | Green et al. | |
| 2012/0022588 A1 | 1/2012 | Berg | |
| 2012/0065677 A1 | 3/2012 | West, Jr. | |
| 2012/0071877 A1 | 3/2012 | Frigg | |
| 2012/0078298 A1 | 3/2012 | Sklar | |
| 2012/0078300 A1 | 3/2012 | Mayer et al. | |
| 2012/0083841 A1 | 4/2012 | DiMatteo et al. | |

OTHER PUBLICATIONS

Brand, Jr., et al., "Graft Fixation Issues in Knee Ligament Surgery," Operative Techniques in Orthopaedics, Oct. 1999, pp. 256-263, vol. 9, No. 4.

Brown et al., "Endoscopic Anterior Cruciate Ligament Reconstruction Using Doubled Gracilis and Semitendinosus Tendons and Endobutton Femoral Fixation," Operative Techniques in Sports Medicine, Oct. 1999, pp. 201-213, vol. 7, No. 4.

Dalton, Jr., et al., "Surgical Techniques to Correct Nonanatomic Femoral Tunnels," Operative Techniques in Sports Medicine, Apr. 1998, pp. 83-90, vol. 6, No. 2.

Drosdowech et al., "Arthroscopic Hamstring Anterior Cruciate Ligament Reconstruction with Endobutton Femoral Fixation," Operative Techniqes in Sports Medicine, Jul. 1996, pp. 147-151, vol. 6, No. 3.

Fithian et al., "Fixation in Knee Ligament Repair and Reconstruction," Operative Techniques in Orthopaedics, Apr. 1992, pp. 63-70, vol. 2, No. 2.

Fulkerson, "Central Quadriceps Free Tendon for Anterior Cruciate Ligament Reconstruction," Operative Techniques in Sports Medicine, Oct. 1999, pp. 195-200, vol. 7, No. 4.

Goitz et al., "Orthopedic Implants: A Guide to Radiographic Analysis," Current Problems in Diagnostic Radiology, Jul./Aug. 1996, pp. 113-168, vol. 25, No. 4.

Graf et al., "Endobutton Fixation of Hamstring Tendon Grafts," Operative Techniques in Sports Medicine, Oct. 1999, pp. 189-194, vol. 7, No. 4.

Hara et al., "A New Arthroscopic Method for Reconstructing the Anterior and Posterior Cruciate Ligaments Using a Single-Incision Technique: Simultaneous Grafting of the Autogenous Semitendinosus and Patellar Tendons," Arthroscopy: The journal of Arthroscopic and Related Surgery, Nov./Dec. 1999, pp. 871-876, vol. 15, No. 8.

Howell et al., "Endoscopic Fixation of a Double-Looped Semiteninosus and Gracilis Anterior Cruciate Ligament Graft Using Bone Mulch Screw," Operative Techniques in Orthopaedics, Jul. 1996, pp. 152-160, vol. 6, No. 3.

Janis et al., "Spike Metallic Washer and Screw for Reattachment of the Achilles Tendon After Repair of a Distal Rupture," The Journal of Foot & Ankle Surgery, Jan./Feb. 2000, pp. 49-53, vol. 39, No. 1.

Kumar et al., "Posterolateral reconstruction of the knee: a tunnel technique for proximal fixation," The Knee, 1999, pp. 257-260, vol. 6.

Larson, "Anterior Cruciate Ligament Reconstruction with Hamstring Tendons," Operative Techniques in Orthopaedics, Jul. 1996, pp. 138-146, vol. 6, No. 3.

Leitman et al., "Quadriceps Tendon Anterior Cruciate Ligament Reconstruction Using the All-Inside Technique," Operative Techniques in Sports Medicine, Oct. 1999, pp. 179-188, vol. 7, No. 4.

MacGillivray et al., "Treatment of Acute and Chronic Injuries to the Posterolateral and Lateral Knee," Operative Techniques in Orthopaedics, Oct. 1999, pp. 309-317, vol. 9, No. 4.

Matthews et al., "Fixation Strengths of Patellar Tendon-Bone Grafts," Arthroscopy: The Journal of Arthroscopic and Related Surgery, Feb. 1993, pp. 76-81, vol. 9, No. 1.

Nakano et al., "Interference screw fixation of double flexor tendon graft in anterior cruciate ligament reconstruction—biomechanical evaluation with cyclic elongation," Clinical Biomechanics, 2000, pp. 188-195, vol. 15.

Petrie et al., "Double Bundle Posterior Cruciate Ligament Reconstruction Technique: University of Pittsburgh Approach," Operative Techniques in Sports Medicine, Jul. 1999, pp. 118-126, vol. 7, No. 3.

To et al., "Contributions of Femoral Fixation Methods to the Stiffness of Anterior Cruciate Ligament Replacements at Implantation," Arthroscopy: The Journal of Arthroscopic and Related Surgery, May/Jun. 1999, pp. 379-387, vol. 15, No. 4.

Trenhaile, "Biceptor Tenodesis System Offers All-Inside Option to Biceps Tendon Repair," Joint Intelligence, at least as early as Apr. 18, 2010, pp. 1-7, vol. 1, Issue 1, Smith & Nephew.

Trout et al., "Rupture of the Tibialis Anterior Tendon," The Journal of Foot & Ankle Sugery, 2000, pp. 54-58, vol. 39, No. 1.

(56) References Cited

OTHER PUBLICATIONS

Veltri et al., "Treatment of Acute and Chronic Injuries to the Posterolateral and Lateral Knee," Operative Techniques in Sports Medicine, Jul. 1996, pp. 174-181, vol. 4, No. 3.
Yamanaka et al., "The Effects of Cyclic Displacement on the Biomechanical Characteristics of Anterior Cruciate Ligament Reconstructions," American Journal of Sports Medicine, Jun. 1999, pp. 772-777, vol. 27, No. 6.

* cited by examiner

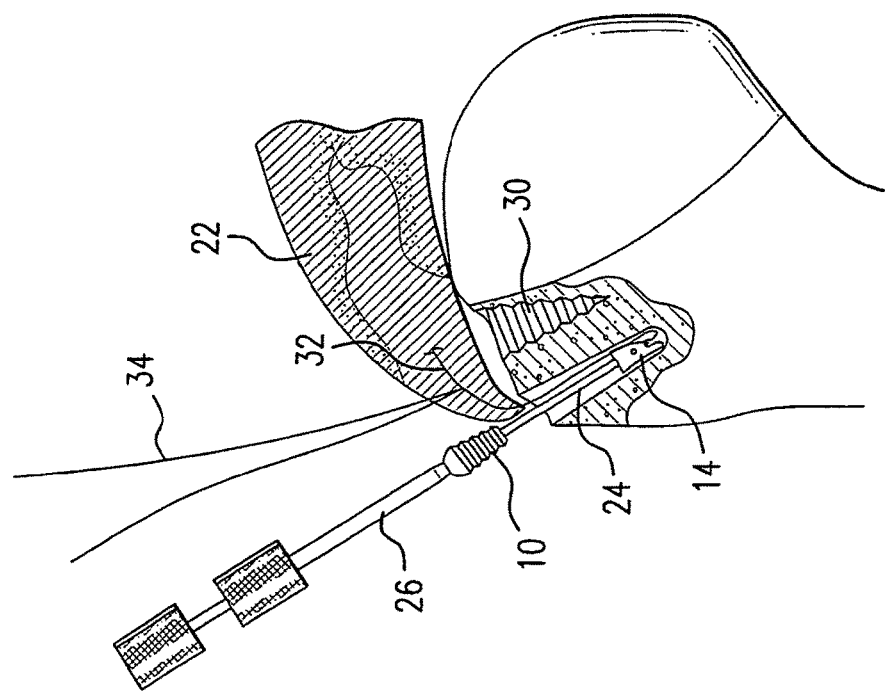
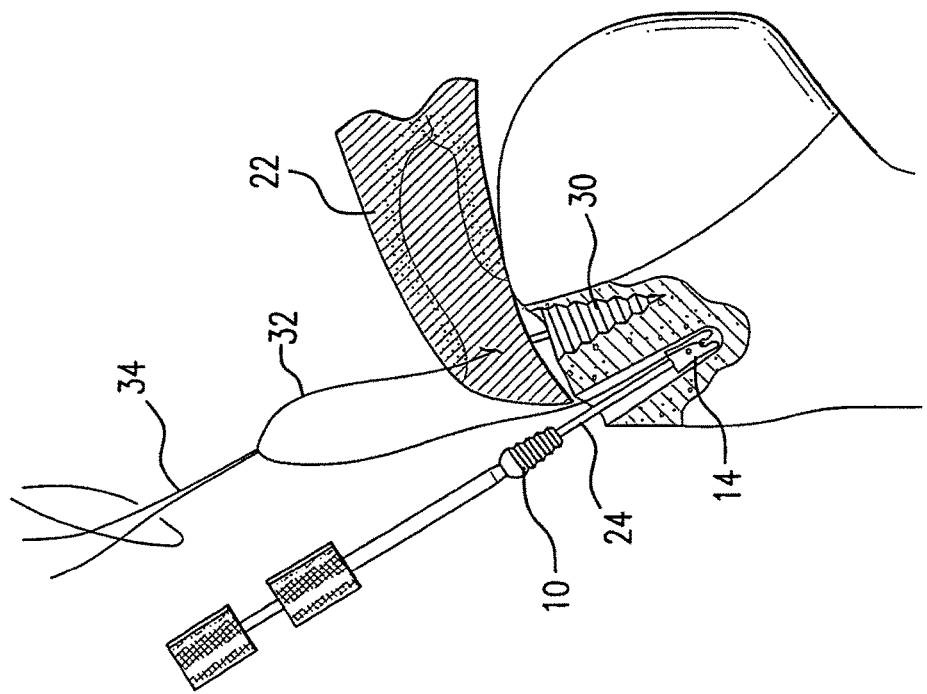
FIG. 5e
FIG. 5f

METHOD FOR SECURING SUTURES TO BONES

CROSS-REFERENCE TO RELATED APPLICATIONS

This application is a divisional of U.S. application Ser. No. 13/252,494, filed Oct. 4, 2011, which is a divisional of U.S. application Ser. No. 12/453,290, filed May 6, 2009 which claims the benefit of U.S. Provisional Application No. 61/071,563, filed May 6, 2008, which are hereby incorporated by reference herein in their entireties, including but not limited to those portions that specifically appear hereinafter, the incorporation by reference being made with the following exception: In the event that any portion of the above-referenced patent applications to which priority is claimed are inconsistent with this application, this application supercedes said above-referenced patent applications.

STATEMENT REGARDING FEDERALLY SPONSORED RESEARCH OR DEVELOPMENT

Not Applicable.

BACKGROUND OF THE INVENTION

During surgery, anchors have been used with sutures to reattach tissue to bone. The anchors have been inserted into holes that have been pre-drilled. Difficulties arise when the anchor has been inserted and is not flush with the top of the bone mass. Additionally, the anchor has been known to move or adjust thereby jeopardizing a secure repair.

SUMMARY OF THE INVENTION

Part of a successful surgery to reconnect tissue to bone requires that sutures firmly secure the tissue to the bone. It is important that the repair have long term stability. The disclosed method, system and device for securing the repair includes an anchor placed within a pre-drilled hole formed in bone and a cannulated screw inserted into the hole after the anchor, and holding same in place, to effectuate a firm and secure connection of tissue to bone, particularly when the quality of the bone does not permit optimal fixation. The method, system and device allows superior screw in fixation with the ease of knotless suture anchor application.

BRIEF DESCRIPTION OF THE DRAWINGS

FIGS. 5*a*-5*i* depict the system and method in a double row rotator cuff repair.

DETAILED DESCRIPTION

Figure 1A:
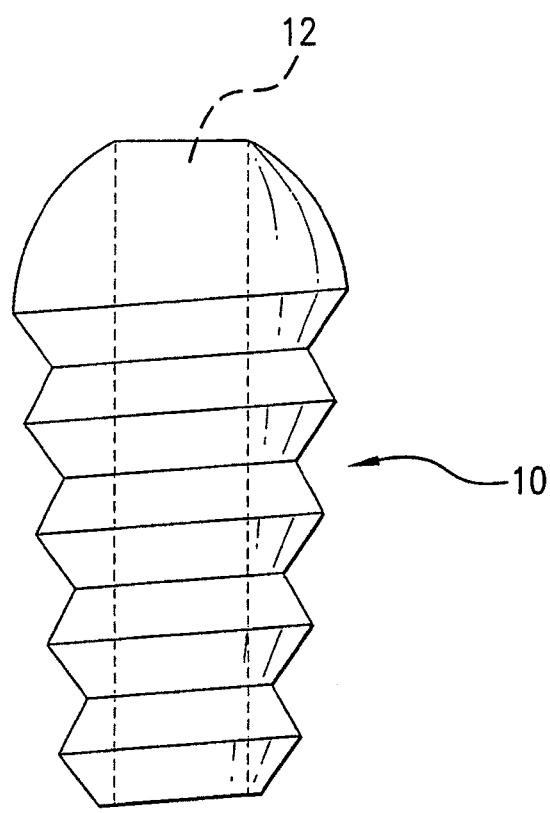
FIG. 1*a* is a view of a cannulated screw used with the system and method.
Figure 1B:
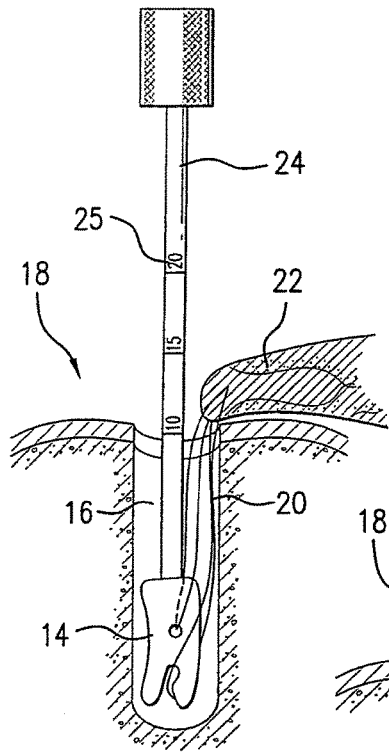
FIGS. 1*b*-1*f* depict steps of the repair.
Figure 1C:
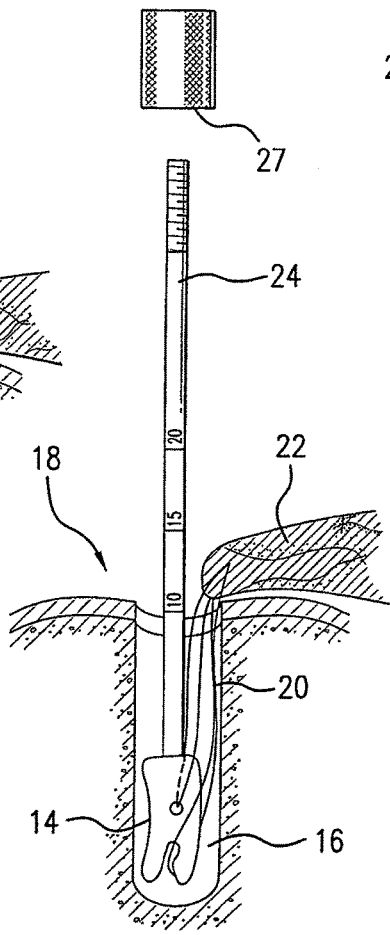
Figure 1D:
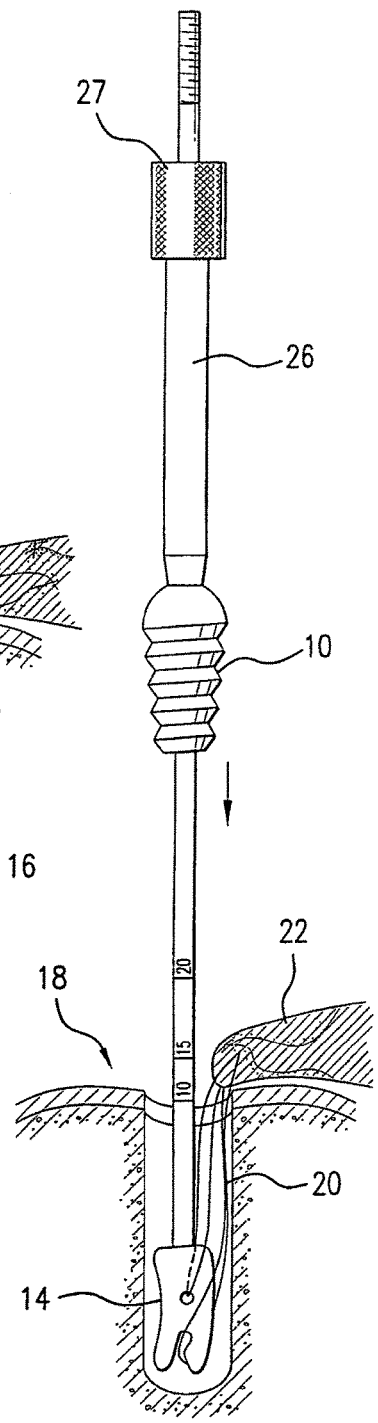
Figures 1E, 1F:
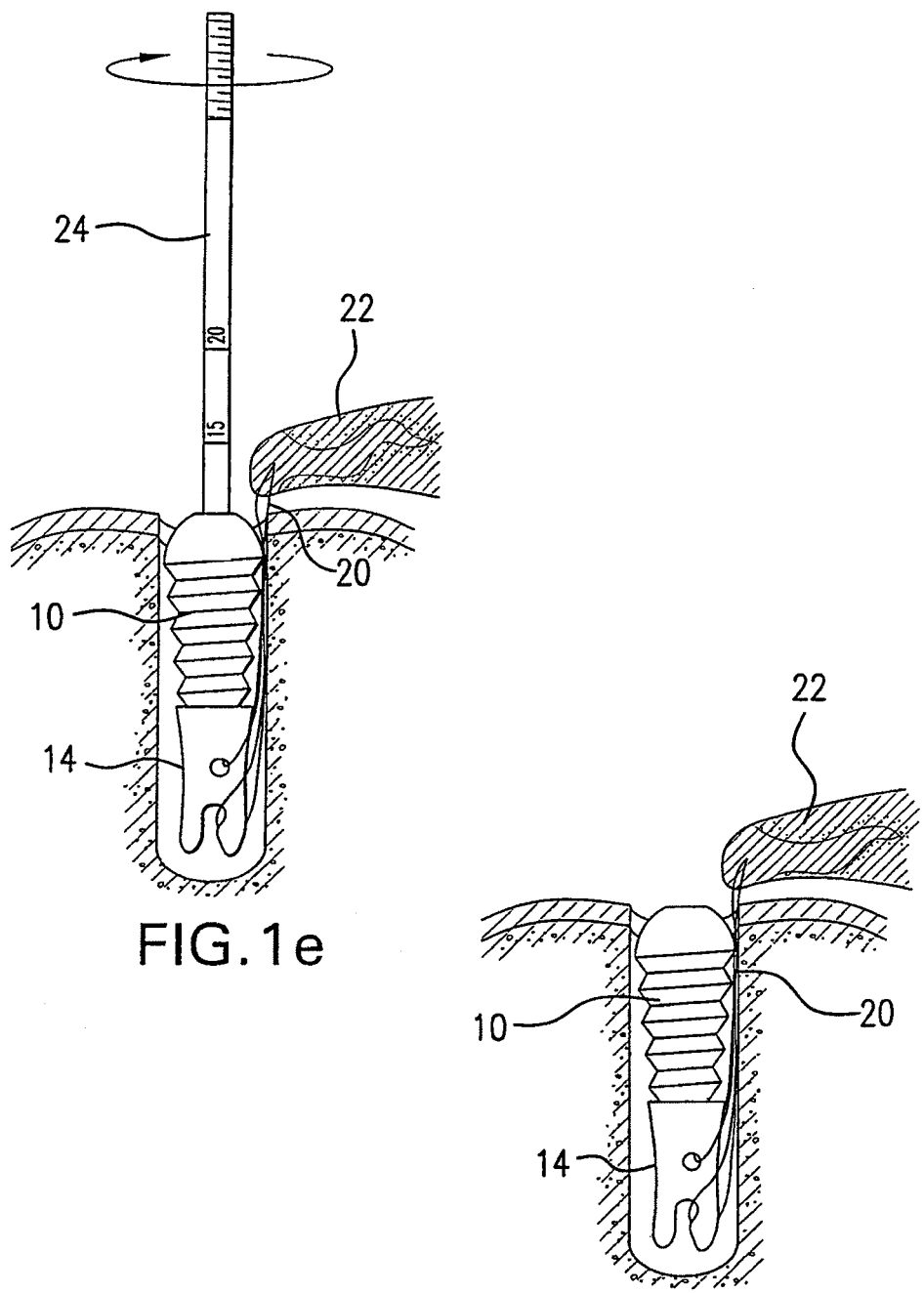

FIG. 1*a* shows the cannulated fastener, such as a cannulated bone screw 10 having a central bore 12 extending the entire length of the screw, allowing the screw to move along a bone anchor inserter rod. The fastener may be made of any suitable material, including bioabsorbable material, and may be a barbed fastener which is driven into a bone hole, rather than screwed. The fastener that is inserted need only have a flattened distal aspect to block the fixation anchor from migrating. In FIG. 1*b*, an anchor 14 has been inserted within a hole 16 in a bone 18. The anchor has a suture loop 20, either fixed or adjustable in length, passing through tissue 22, such as a rotator cuff, to secure the tissue 22 to the bone 18. The anchor has captured the loop, allowing for fixation without needing to tie a knot. As can be seen, there is a distance between the top of the anchor and the top of the opening in the bone. This distance can be measured by markings 25 along the inserter rod 24 seen in FIG. 1*c*. In FIG. 1*d*, the cannulated screw 10 is movable along the inserter rod 24, as is the cannulated screw driver 26. The screw driver 26 allows the screw 10 to be driven into the bone hole 16 as the end of the screw driver engages the head of the screw to rotate the screw. FIG. 1*e* shows the screw 10 having been successfully driven into the hole and now on top of the bone anchor 14 to prevent the anchor's movement. Having been successfully accomplished, the inserter rod 24 is removed as seen in FIG. 1*f*. The standard knotless anchor inserter rod is modified to have a reverse threaded tab 27. This enables the tab to be removed without removing the inserter rod from the anchor.

Figure 2A:
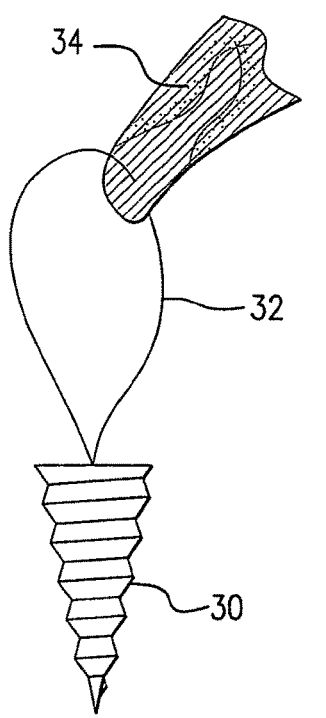
FIGS. 2*a* and 2*b* show different types of anchors used with a multirow repair.
Figure 2B:
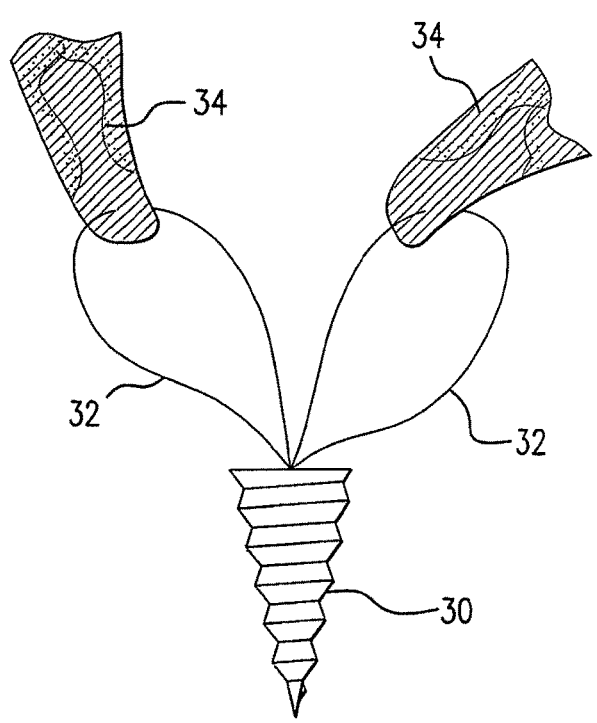
Figure 3:
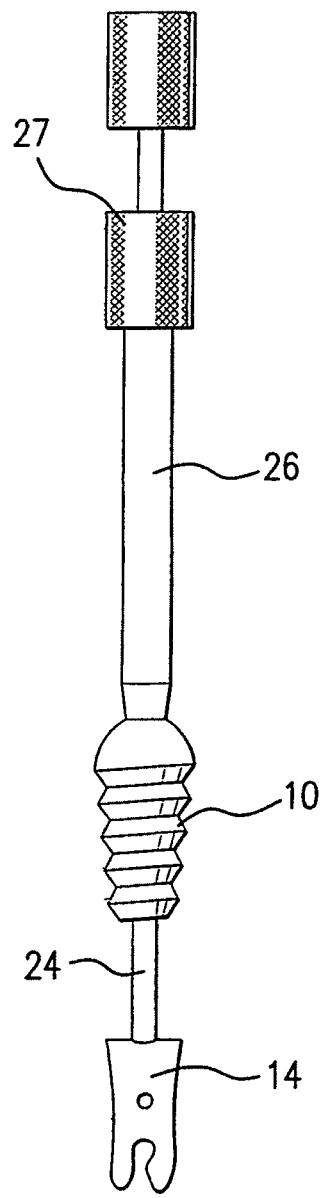
FIG. 3 is a view of the inserter rod, screw and anchor.

FIGS. 2*a* and 2*b* depict just one of the many types of bone anchors 30 that may be used with a double row repair. The bone anchor may accommodate one or multiple suture loops 32 which may be either of fixed or adjustable length. Utility sutures extend from the suture loops. FIG. 3 shows the entire assembly of the inserter rod 24, a bone anchor 14 such as a knotless bone anchor and a cannulated screw 10 and screw driver 26 placed over and movable along the inserter rod.

Figures 4A, 4B:
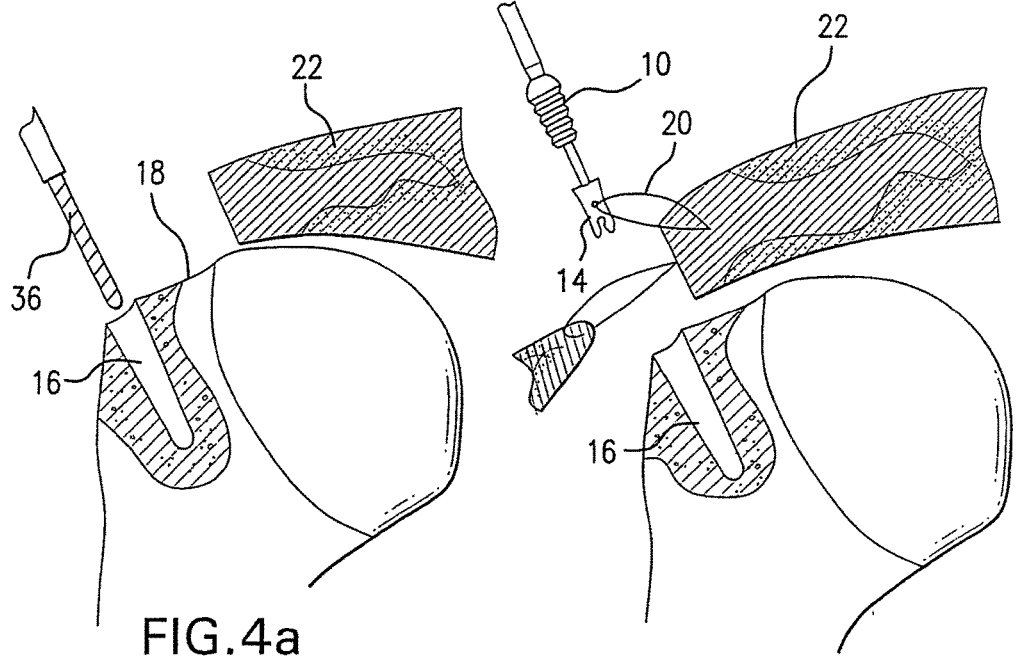
FIGS. 4*a*-4*h* depict the method in a single row rotator cuff repair.
Figure 4C:
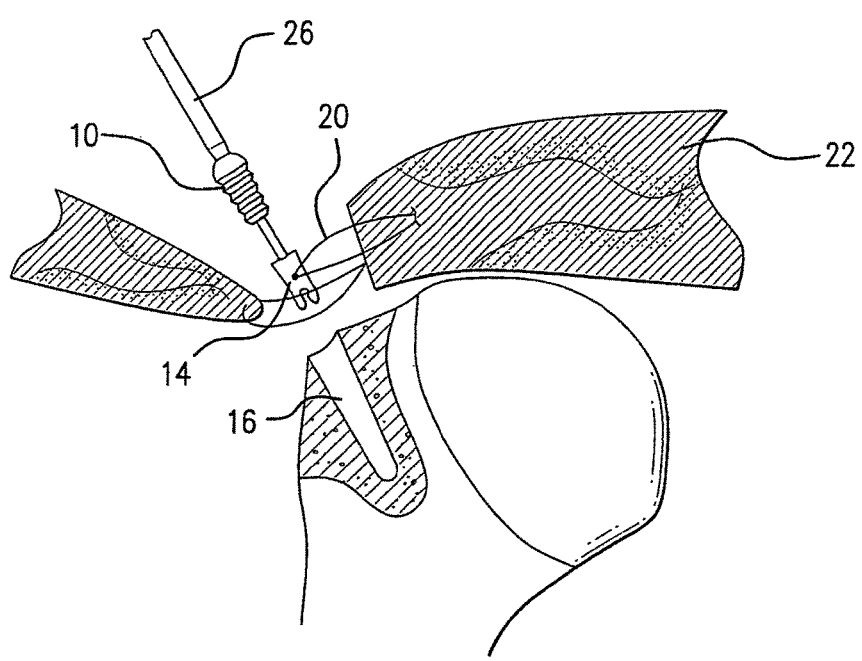
Figures 4D, 4E:
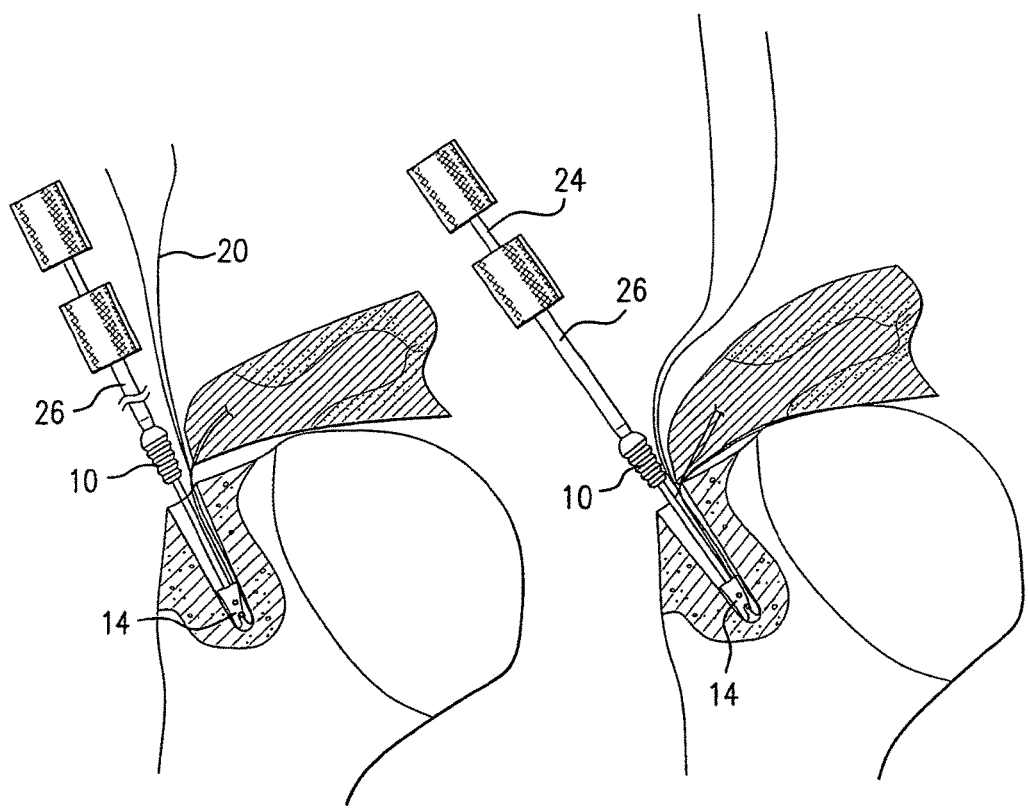
Figure 4F:
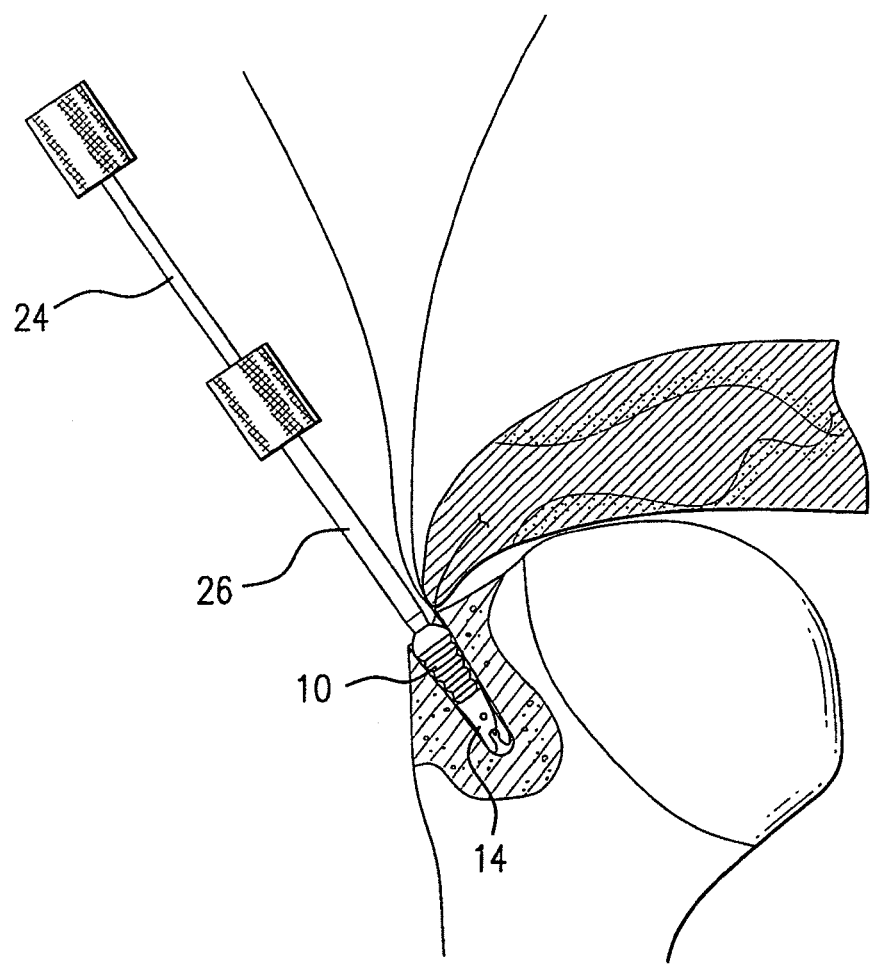
Figure 4G:
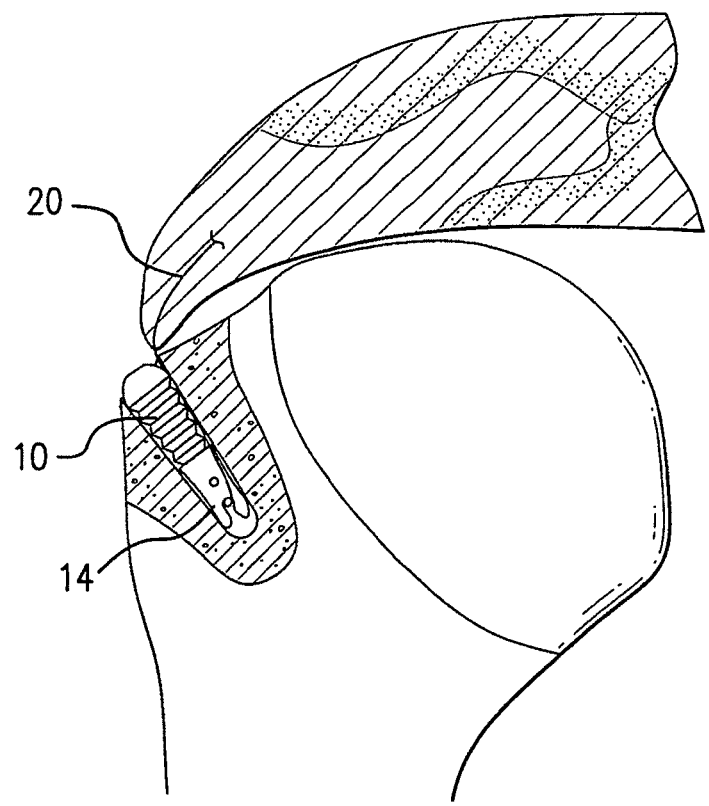
Figure 4H:
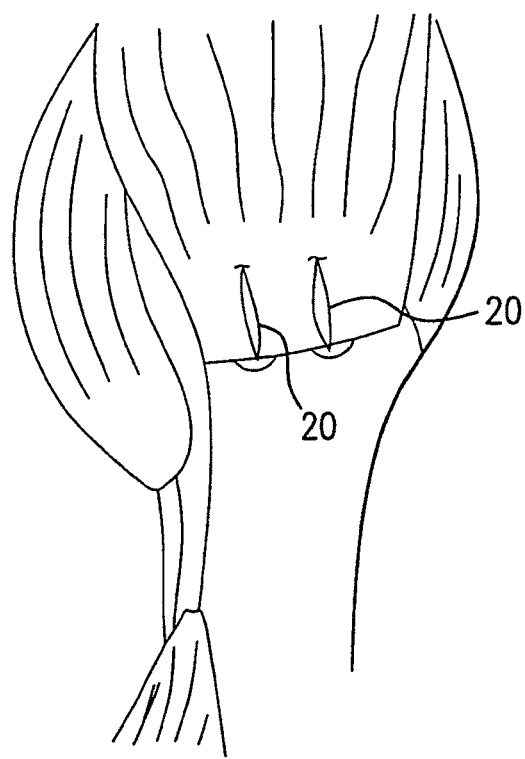

FIGS. 4*a*-4*h* depict a single row rotator cuff repair. A lateral hole 16 is made, by either drilling, or is produced with an awl-like device 36, in the bone 18, as shown in FIG. 4*a* and a suture 20 is passed through the tissue 22. The suture 20 is captured by the bone anchor 14, as seen in FIGS. 4*b* and 4*c*. The anchor 14 is inserted to the appropriate depth 16 and the suture loop is tightened in order to approximate the tissue to the repair site. The loop need not be tightened when the loop is of a fixed length. Once the anchor 14 is successfully seated within the hole, the screw 10 is advanced along the inserter rod 24 and driven into the hole by the cannulated screw driver 26 as seen in FIG. 4*f*. Once successfully inserted, the inserter rod 24 is removed and the repair is complete as seen in FIG. 4*g*. FIG. 4*h* shows a completed two anchor repair.

Figure 5A:
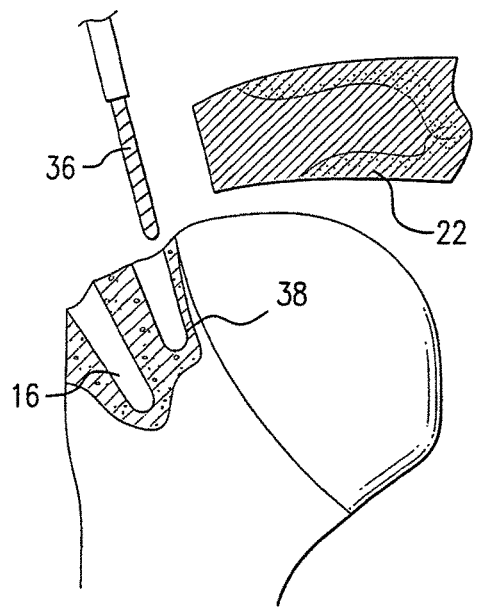
Figure 5B:
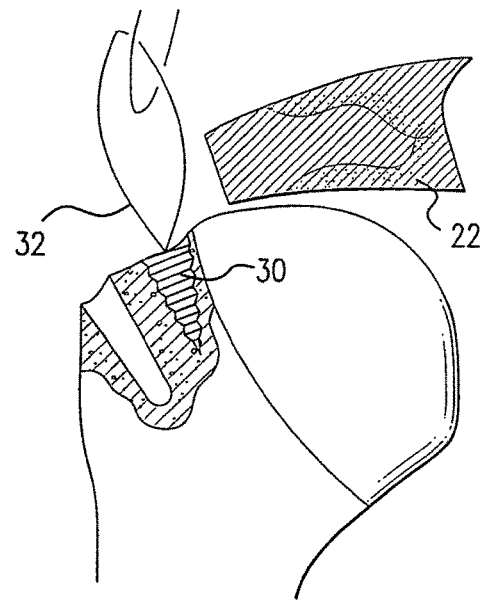
Figure 5C:
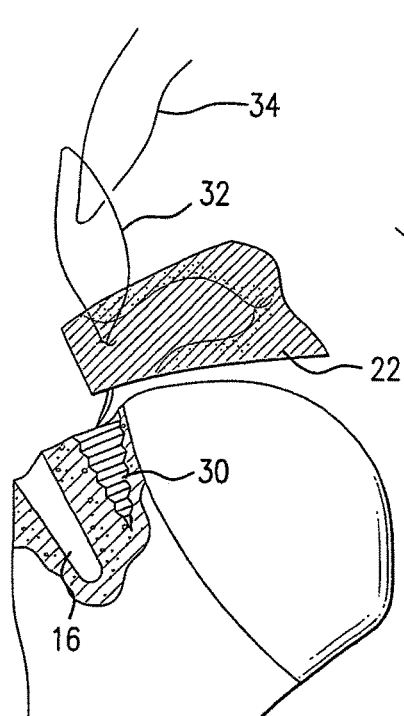
Figure 5D:
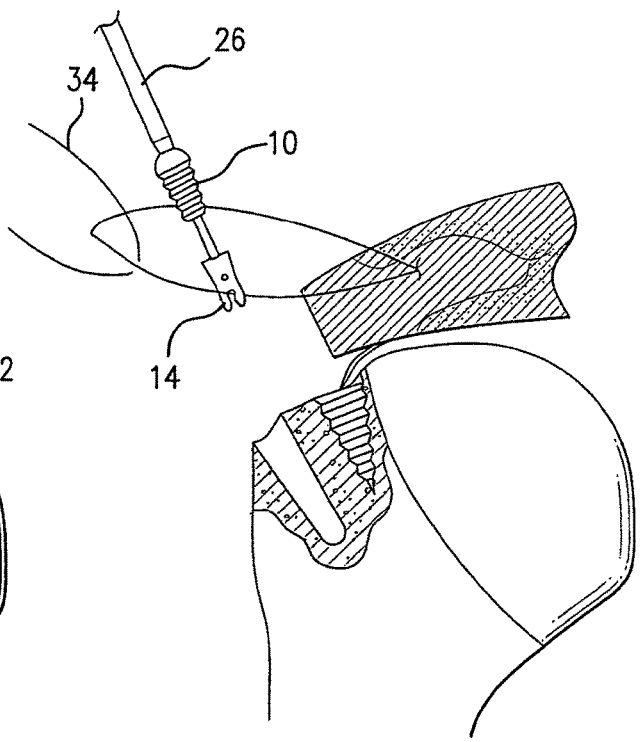
Figure 5G:
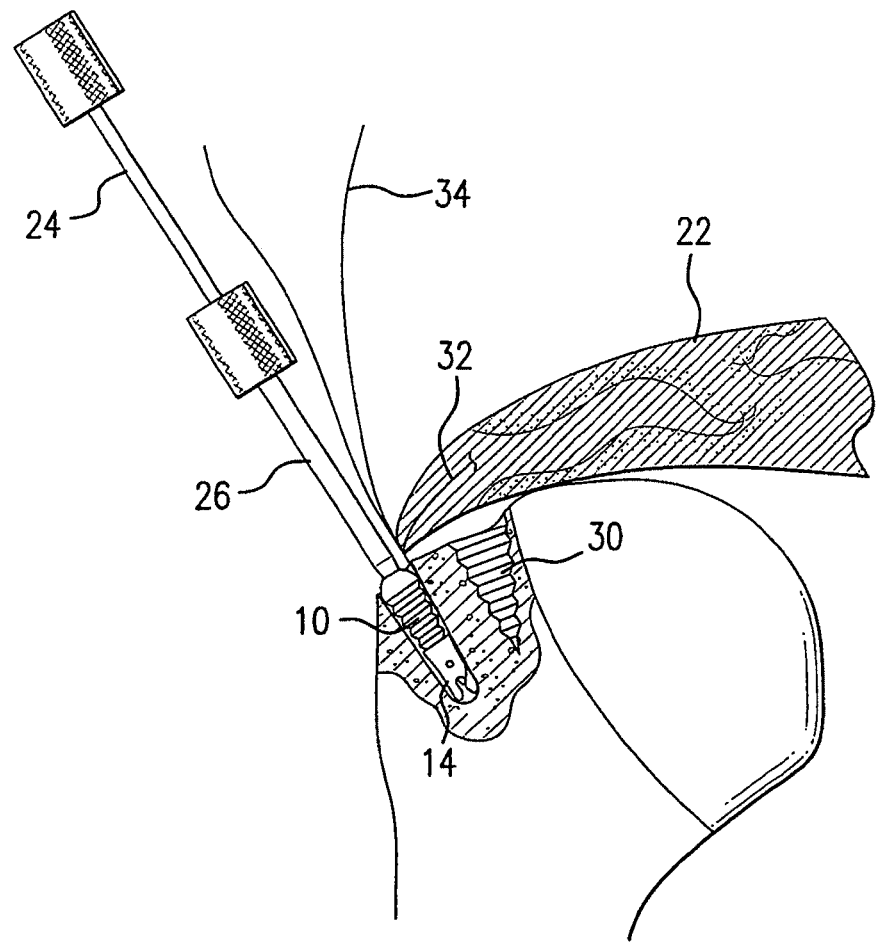
Figure 5H:
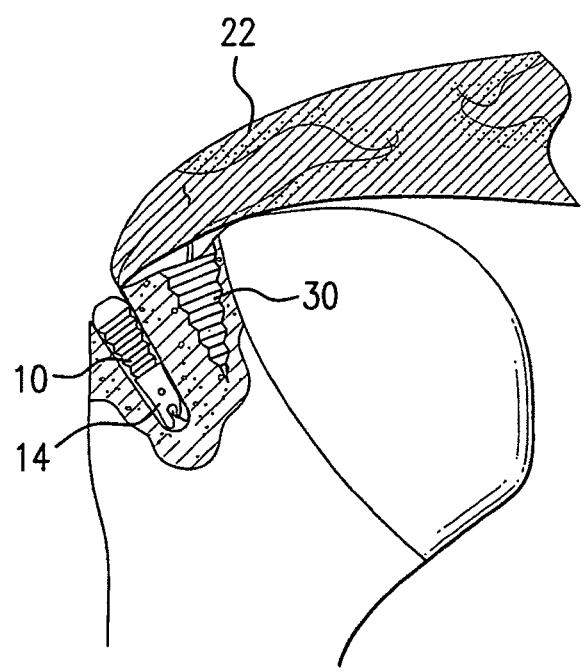
Figure 5I:
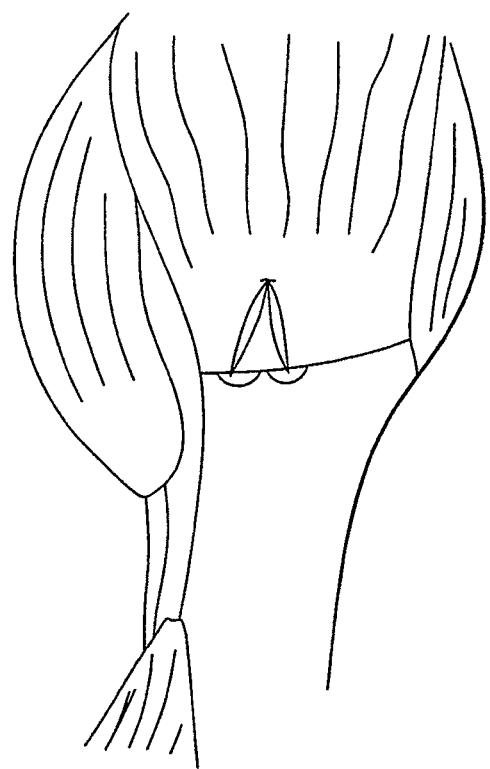

FIGS. 5*a*-5*i* depict a double row repair with a spiral bone anchor 30 with attached suture loop(s) 32, such as the anchors seen in FIGS. 2*a* and 2*b*, driven into a first hole 38. The suture passes through tissue 22 and is captured by the bone anchor 14 as seen in FIG. 5*d*. At this point, the anchor 14 is set within the second hole 16, followed by the setting of the bone screw 10 in a manner described earlier with reference to the single row repair. The completed multiple row repair is depicted in FIG. 5*i*.

The method can be applied to any repair requiring tissue to be reattached to bone. Further, the bone anchor, or cannulated bone screw can be made of any desirable material and may be of bioabsorbable or bioreplaceable material. Either implanted device may change over time.

What is claimed is:

1. An apparatus for anchoring a flexible member into a pre-drilled bore in a bone, said apparatus comprising:
    an anchor having a body member and a pair of legs, each of the pair of legs extending from the body member and terminating at a free end, the anchor comprising a substantially planar top surface formed on the body member opposite the pair of legs, the anchor also including a hole extending in a direction substantially perpendicular with the pair of legs, the hole being distal to the substantially planar top surface;

the pair of legs defining a straddle for receiving the flexible member; and a cannulated bone screw for securing the apparatus in the pre-drilled bore of the bone such that the flexible member is permanently held within the straddle, wherein the cannulated bone screw abuts the anchor such that the cannulated bone screw rotates independently from the anchor when securing the apparatus in the pre-drilled bore.

2. The apparatus of claim 1, wherein the cannulated bone screw comprises a plurality of threads.

3. The apparatus of claim 1, wherein the substantially planar top surface formed on the body member is configured and adapted to receive a distal end of the cannulated bone screw.

4. The apparatus of claim 1, wherein the anchor is configured and adapted to be installed on an end of an inserter rod.

5. The apparatus of claim 1, wherein the cannulated bone screw is configured and adapted to be installed on an end of a driver.

6. The apparatus of claim 1, wherein the flexible member is a suture.

7. The apparatus of claim 1, wherein the substantially planar top surface is characterized by an absence of any protrusions.

8. The apparatus of claim 1, wherein the substantially planar top surface is characterized by an absence of any protrusions extending upwardly from said surface opposite in direction from the pair of legs extending from the body member.

9. The apparatus of claim 1, wherein the cannulated bone screw comprises a cannula configured and dimensioned to allow passage of an inserter rod.

10. The apparatus of claim 1, wherein the anchor is configured and adapted to be rotatably installed on an end of an inserter rod.

11. The apparatus of claim 1, wherein the hole in the anchor receives a suture.

12. An apparatus for anchoring a flexible member into a pre-drilled bore in a bone, said apparatus comprising:

an anchor having a body member and a pair of legs, each of the pair of legs extending from the body member and terminating at a free end, the anchor comprising a substantially planar top surface formed on the body member opposite the pair of legs;

the pair of legs defining a straddle for receiving the flexible member;

a cannulated bone screw for securing the apparatus in the pre-drilled bore of the bone such that the flexible member is permanently held within the straddle, wherein the cannulated bone screw abuts the substantially planar top surface of the anchor such that the cannulated bone screw rotates independently from the anchor when securing the apparatus in the pre-drilled bore;

an insertion rod configured to matingly engage with the anchor, the anchor also including a hole extending in a direction substantially perpendicular with the insertion rod when matingly engaged with the anchor, the hole being distal to the substantially planar top surface and configured to receive a suture or other flexible member; and a cannulated screw driver configured to matingly engage with the cannulated bone screw.

13. The apparatus of claim 12, wherein the substantially planar top surface formed on the body member is configured and adapted to receive a distal end of the cannulated bone screw.

14. The apparatus of claim 12, wherein the anchor is configured and adapted to be installed on a terminal end of the insertion rod.

15. The apparatus of claim 12, wherein the cannulated bone screw is configured and adapted to be installed on an end of the cannulated screw driver.

16. The apparatus of claim 12, wherein the flexible member is a suture.

17. The apparatus of claim 12, where the substantially planar top surface is characterized by a lack of any protrusions.

18. The apparatus of claim 12, wherein the cannulated bone screw comprises a cannula configured and dimensioned to allow passage of the insertion rod.

19. The apparatus of claim 12, wherein the insertion rod comprises a handle.

20. The apparatus of claim 12, wherein the cannulated screw driver comprises a handle.

21. The apparatus of claim 12, wherein the hole in the anchor receives a suture.

22. An apparatus for anchoring a flexible member into a pre-drilled bore in a bone, said apparatus comprising:

an anchor having a body member and a pair of legs, each of the pair of legs extending from the body member and terminating at a free end, the anchor comprising a substantially planar top surface formed on the body member opposite the pair of legs, wherein the anchor includes a hole extending in a direction substantially perpendicular with the pair of legs, the hole being distal to the substantially planar top surface and configured to receive a suture or other flexible member;

the pair of legs defining a straddle for receiving the flexible member;

a cannulated bone screw for securing the apparatus in the pre-drilled bore of the bone such that the flexible member is permanently held within the straddle, wherein a distal end of the cannulated bone screw abuts the substantially planar top surface of the anchor such that the cannulated bone screw rotates independently from the anchor when securing the apparatus in the pre-drilled bore;

an insertion rod configured to matingly engage with the anchor;

a cannulated screw driver configured to matingly engage with the cannulated bone screw;

wherein the cannulated bone screw comprises a plurality of threads and an exterior surface generally tapering in a proximal-to-distal direction;

wherein the substantially planar top surface formed on the body member is configured and adapted to receive the distal end of the cannulated bone screw;

wherein the anchor is configured and adapted to be installed on a terminal end of the insertion rod;

wherein the cannulated bone screw is configured and adapted to be installed on an end of the cannulated screw driver;

wherein the flexible member is a suture;

wherein the substantially planar top surface is characterized by a lack of any protrusions;

wherein the cannulated bone screw comprises a cannula configured and dimensioned to allow passage of the insertion rod;

wherein the insertion rod comprises a handle;

wherein the cannulated screw driver comprises a handle.

23. An apparatus for anchoring a flexible member into a pre-drilled bore in a bone, said apparatus comprising:

an anchor having a body member and a pair of legs, each of the pair of legs extending from the body member and terminating at a free end, the anchor comprising a substantially planar top surface formed on the body member opposite the pair of legs, the anchor also including a hole extending in a direction substantially perpendicular with the pair of legs, the hole being distal to the substantially planar top surface and configured to receive a suture or other flexible member;

the pair of legs defining a straddle for receiving the flexible member; and a cannulated bone screw for securing the apparatus in the pre-drilled bore of the bone such that the flexible member is permanently held within the straddle, wherein the cannulated bone screw abuts the anchor such that the cannulated bone screw rotates independently from the anchor when securing the apparatus in the pre-drilled bore, and the cannulated bone screw includes an exterior surface generally tapering in a proximal-to-distal direction.

\* \* \* \* \*